United States Patent
Lee et al.

(10) Patent No.: US 7,951,333 B2
(45) Date of Patent: May 31, 2011

(54) CENTRIFUGAL FORCE-BASED MICROFLUIDIC DEVICE FOR PROTEIN DETECTION AND MICROFLUIDIC SYSTEM INCLUDING THE SAME

(75) Inventors: Beom Seok Lee, Hwaseong-si (KR); Yoon Kyoung Cho, Suwon-si (KR); Jeong Gun Lee, Seoul (KR); Jong-myeon Park, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 12/851,819

(22) Filed: Aug. 6, 2010

(65) Prior Publication Data
US 2011/0020194 A1    Jan. 27, 2011

Related U.S. Application Data

(63) Continuation-in-part of application No. 11/850,129, filed on Sep. 5, 2007, now Pat. No. 7,776,267.

(30) Foreign Application Priority Data

Sep. 5, 2006   (KR) .................. 10-2006-0085372
Jan. 11, 2007  (KR) .................. 10-2007-0003401

(51) Int. Cl.
*G01N 9/30*    (2006.01)
(52) U.S. Cl. ........ 422/72; 435/287.1; 436/177; 422/68.1
(58) Field of Classification Search .................. 422/72
See application file for complete search history.

(56) References Cited

U.S. PATENT DOCUMENTS

| | | | |
|---|---|---|---|
| 6,632,399 B1 * | 10/2003 | Kellogg et al. | 422/72 |
| 2002/0027133 A1 | 3/2002 | Kellogg et al. | |
| 2005/0136545 A1 * | 6/2005 | Schmid et al. | 436/45 |
| 2006/0219308 A1 * | 10/2006 | Oh et al. | 137/827 |
| 2008/0042096 A1 * | 2/2008 | Park et al. | 251/368 |
| 2009/0035746 A1 * | 2/2009 | Ehben et al. | 435/4 |

FOREIGN PATENT DOCUMENTS
WO    02/42498 A2    5/2002
WO    WO 0242498 A2 *  5/2002

OTHER PUBLICATIONS

European Search Report, dated Sep. 24, 2010 issued in counterpart European Application No. 10169799.3.

* cited by examiner

*Primary Examiner* — In Suk Bullock
*Assistant Examiner* — Jennifer Wecker
(74) *Attorney, Agent, or Firm* — Sughrue Mion, PLLC

(57) ABSTRACT

A centrifugal force-based microfluidic device for the detection of a target biomolecule and a microfluidic system including the same are provided. The device includes a body of revolution; a microfluidic structure disposed in the body of revolution including chambers, channels connecting the chambers, and valves disposed in the channels to control fluid flow, the microfluidic structures transmitting fluid using centrifugal force due to rotation of the body of revolution; and beads disposed in the microfluidic structures, the beads having capture probes on the surfaces thereof which are selectively bonded with target protein; and a detection probe disposed in the microfluidic structures and selectively bonded to the target protein, and which includes a material required to express an optical signal, wherein the microfluidic structure mixes the beads, biological samples, and the detection probe to react and washes and separates the beads after the reaction.

12 Claims, 17 Drawing Sheets
(10 of 17 Drawing Sheet(s) Filed in Color)

OPEN VALVE

BEADS MOVES TO
MIXING CHAMBER

BEADS ARE MIXING WITH SERUM
Anti-HBs IS CAPTURED ON BEAD SURFACES

BEADS ARE SEDIMENTED
ON THE BOTTOM PART

OPEN VALVE    MIXING RESIDUE IN
              WASTE CHAMBER

CLOSE THE CHANNEL BY
HEATING THE CLOSING VALVE

OPEN VALVE

WASHING BUFFER IS MOVED
TO MIXING CHAMBER

BEADS ARE SEDIMENTED
ON THE BOTTOM PART

OPEN VALVE

MIXING RESIDUE IN WASTE CHAMBER

OPEN VALVE

BEADS ARE SEDIMENTED ON THE BOTTOM PART AND METERRED

OPEN VALVE

BEADS ARE SEDIMRNTED ON THE
BOTTOM PART AND MIXED WITH SUBSTRATE

SET ROI FOR DETECTION OF
BLUE COLOR BY COLOR CCD

CENTRIFUGAL FORCE-BASED MICROFLUIDIC DEVICE FOR PROTEIN DETECTION AND MICROFLUIDIC SYSTEM INCLUDING THE SAME

CROSS-REFERENCE TO RELATED PATENT APPLICATION

This application is a continuation application of U.S. application Ser. No. 11/850,129, filed Sep. 5, 2007 (now allowed), which claims the benefit of Korean Patent Application Nos. 10-2006-0085372, filed on Sep. 5, 2006 and 10-2007-0003401, filed Jan. 11, 2007, in the Korean Intellectual Property Office, the disclosures of which are incorporated herein in their entirety by reference.

BACKGROUND OF THE INVENTION

1. Field of the Invention

The present invention relates to a centrifugal force-based microfluidic device which controls fluid flow by centrifugal force in a microfluidic structure prepared on a body of revolution. The present invention also relates to a centrifugal force-based microfluidic device for detecting target protein from a biological sample.

2. Description of the Related Art

In general, a microfluidic structure constituting a microfluidic device may include a chamber, a channel, a valve, and a plurality of functional units, wherein the chamber stores a small amount of fluid, the fluid flows through the channel, the valve controls fluid flow, and the functional units receive the fluid to perform certain functions. This microfluidic structure, which is formed on a chip-type substrate for conducting experiments including a biochemical reaction, is referred to as a bio-chip. In particular, a device manufactured to perform several steps of processes and operations in one chip is referred to as a lab-on-a chip.

In order to transfer fluid in the microfluidic structure, driving pressure is needed. Capillary pressure and pressure by an additional pump may be used as the driving pressure. Recently, centrifugal force-based microfluidic devices in which microfluidic structures are disposed on a compact disk (CD)-type body of revolution have been suggested. Such a device is referred to as a Lab CD. However, in this case, since a body of revolution is not fixed onto a frame and thus moves, it is difficult to control fluid flow and temperature of the functional units in the body of revolution.

SUMMARY OF THE INVENTION

The present invention provides a centrifugal force-based microfluidic device including a microfluidic structure and a microfluidic system including the microfluidic device and devices to operate the microfluidic device. The microfluidic device can detect presence of target protein, through a series of processes performed in the microfluidic structure such as moving biomaterial samples using centrifugal force when the biomaterial samples such as blood are injected into the microfluidic structures prepared on a body of revolution.

According to an aspect of the present invention, there is provided a centrifugal force-based microfluidic device for biomolecule detection, including: a body of revolution a body of revolution having a rotation center and a circumference; a microfluidic structure disposed in the body of revolution comprising a plurality of chambers, channels connecting the chambers to each other and forming a path of fluid flow between the chambers, and valves disposed in the channels to control the fluid flow between the chambers, the microfluidic structure transmitting fluid using centrifugal force due to rotation of the body of revolution, wherein one of the plurality of chambers receives a fluid biological sample beads disposed in the microfluidic structure, the beads having a first probe to capture a target molecule from a fluid biological sample, the first probe selectively binds to the target molecule; and a second probe disposed in the microfluidic structure and selectively binding to the target molecule, and which comprises a substance emitting an optical signal, wherein the microfluidic structure mixes the beads, the biological sample, and the second probe to bring them into contact with each other to produce a bead-target molecule-second probe complex, if the fluid biological sample contains the target molecule; and separates the bead-target molecule-second probe complex.

The microfluidic device may further include a substrate solution contained in the microfluidic structure, wherein the substrate solution is brought into contact with the bead-target molecule-second probe complex to generate an optical signal. That is, the optical signal emission materials may generate an optical signal independently such as fluorescence and color or may generate an optical signal by a reaction of a substrate and an enzyme included in the substrate solution.

The valves may be selected from the group consisting of a capillary valve, a hydrophobic valve, a mechanical valve, and a phase-change valve. Here, each of the valves may include a phase-change valve, the phase-change valve which comprises a valve plug in which heat generating particles and phase-change materials are included, wherein the heat generating particles absorb electromagnetic waves from an external energy source and the phase-change material is melted by heat generated from the heat generating particles, and controls the fluid flow in the channels, by opening or closing the channels. The phase-change valve may include an opening valve which is disposed to close the channel at an initial stage, wherein the valve plug is melted by heat generated by the heat generating particles, thereby opening the channel. The phase-change valve may include a closing valve which is disposed in a valve chamber connected to the channel which is opened at an initial stage, wherein the valve plug is melted and expanded by heat generated by the heat generation particles to flow into the channel, thereby closing the channel.

According to another aspect of the present invention, there is provided a microfluidic device including: a body of revolution having a rotation center and a circumference; a microfluidic structure disposed in the body of revolution comprising a plurality of chambers, channels connecting the chambers to each other and forming a path of fluid flow between the chambers, and valves disposed in the channels to control the fluid flow, the microfluidic structures transmitting fluid using centrifugal force due to rotation of the body of revolution, wherein one of the plurality of chambers receives a fluid biological sample; beads having a first probe to capture a target molecule from a fluid biological sample, the first probe selectively binds to the target molecule; and a second probe selectively binding to the target molecule and including a substance emitting an optical signal, wherein the microfluidic structure comprises: a sample chamber which receives a sample solution containing the fluid biological sample; a buffer chamber which receives a buffer solution; a bead chamber which receives a bead solution containing the beads; a mixing chamber which is fluid connected to the sample chamber, the buffer chamber, and the bead chamber through the channel; which receives a solution containing the second probe; which comprises an inlet to receive a fluid and an outlet to discharge the fluid, the outlet being disposed with a greater distance from the rotation center of the body of revolution than the inlet, and the outlet being provided with a valve to control a flow of the fluid discharged from the mixing chamber; and in which the sample and the beads are brought into contact with each other to produce a bead-target molecule-second probe complex, if the fluid biological sample contains the target molecule; and separates the bead-target molecule-second probe complex; a waste chamber which is fluid connected to the outlet of the mixing chamber through a channel, the waste chamber receiving the fluid discharged from the mixing chamber by changes of phases of a valve; and an optical signal emission chamber connected to the outlet of the mixing chamber through a channel, in which a substrate solution is brought into contact with the bead-target molecule-second probe complex to generate an optical signal.

The mixing chamber may be disposed with a greater distance from the center of the body of revolution than the sample chamber, the buffer chamber, and the bead chamber and is disposed with a smaller distance from the center of the body of revolution than the waste chamber and the optical signal emission chamber. The channel connecting the mixing chamber and the waste chamber may be connected such that a space can be provided in the channel where the beads can be collected between a part connected to the channel and the outlet of the mixing chamber.

The channel connecting the mixing chamber and the waste chamber may include a valve which can open and close, In this case, the channel connecting the mixing chamber and the waste chamber can open and close at least two times.

The channels connecting the buffer chamber and the mixing chamber may be connected corresponding to various levels of the fluid in the buffer chamber and each channel may include valves, each of which is operated, independently.

In this case, as a number of water levels, a number of openings and closings of the channel connecting the mixing chamber and the waste chamber is determined.

The microfluidic device may further include magnetic field forming materials which are disposed at a location which allows the optical signal emission chamber to draw and concentrate the magnetic beads contained in the optical signal emission chamber by magnetic force of the magnetic field forming materials.

In addition, the microfluidic device may further include a centrifuging unit connected to a channel which connects the sample chamber and the mixing chamber, the centrifuging unit centrifuging the fluid biological sample contained in the sample chamber, prior to discharging the fluid biological sample into the mixing chamber.

In the microfluidic device, the optical signal emission chamber receives the substrate solution, which is brought into contact with the bead-target molecule-second probe complex to generate an optical signal.

Each of the valves may be selected from the group consisting of a capillary valve, a hydrophobic valve, a mechanical valve, and a phase-change valve.

Here, each of the valves may include a phase-change valve, the phase-change valve comprising a valve plug in which heat generating particles and phase-change materials are included, wherein the heat generating particles absorb electromagnetic waves from an external device and the phase-change material is melted by heat generated from the heat generating particles, and controlling fluid flow, wherein the fluid passes through the channels, according to a position of the valve plug in the channels.

The phase-change valve may include an opening valve which is disposed to close the channel at an initial stage, wherein the valve plug prepared after the valve plug is melted by heat generated by the heat generation particles, thereby opening the channel. The phase-change valve may include a closing valve which is disposed in a valve chamber connected to the channel which is opened at an initial stage, wherein the valve plug is melted and expanded by heat generated by the heat generation particles, thereby closing the channel.

According to another aspect of the present invention, there is provided a microfluidic system including: a centrifugal force-based microfluidic device as described above; a rotation operating unit which rotates the body of revolution of the microfluidic device; and a light detecting unit which detects an optical signal of the microfluidic device.

The microfluidic system may further include a substrate solution contained in the microfluidic structure, wherein the substrate solution is bought into contact with the bead-target-molecule-second probe complex to generate an optical signal.

Each of the valves may be selected from the group consisting of a capillary valve, a hydrophobic valve, a mechanical valve, and a phase-change valve.

The microfluidic system may further include an external energy source which irradiates electromagnetic waves onto a region selected on the microfluidic device.

Here each of the valves may include a phase-change valve which comprises a valve plug in which heat generating particles and phase-change materials are included, wherein the heat generating particles absorb an electromagnetic wave from an external device and the phase-change material is melted by heat generated from the heat generating particles, and controls the flow of fluid in the channels by opening or closing the channels.

According to another aspect of the present invention, there is provided a microfluidic system including: the microfluidic device described above, a rotation operating unit which rotates the body of revolution of the microfluidic device; and a light detecting unit which detects an optical signal of the microfluidic device.

The microfluidic system may further include an external energy source which irradiates electromagnetic waves onto a region of the microfluidic device. Here, each of the valves may include a phase-change valve, which comprises a valve plug in which heat generating particles and phase-change materials are included, wherein the heat generating particles absorb an electromagnetic wave from an external energy source and the phase-change material is melted by heat generated from the heat generating particles, and controls the flow of fluid in the channels, by opening or closing the channels.

According to another aspect of the present invention, there is provided a microfluidic system including: a body of revolution provided with a rotational axis and a circumference; a microfluidic structure disposed in the body of revolution comprising a plurality of chambers, channels connecting the chambers to each other and valves disposed in the channels to control fluid flow, the microfluidic structures transmitting fluid using centrifugal force due to rotation of the body of revolution, wherein one of the plurality of chambers receives a fluid biological sample; magnetic beads included in any one of the chambers which selectively capture a target molecule from the fluid biological sample flowing into the corresponding chamber; a revolution plate formed to be integral with the body of revolution on one side of the body of the revolution, the revolution plate being provided with a rotation axis and a circumference which each correspond to the rotational axis and the circumference of the body of the revolution; a guide rail disposed in the revolution plate which has a form of a path to connect various positions having each different distance from the rotational axis of the revolution plate and includes a magnet therein so as to move the magnet; and an external magnet disposed outside of the revolution plate to be temporarily fixed to at least a specific position corresponding to any one of the positions in the guide rail, wherein the microfluidic structure includes: a sample chamber which receives a sample solution; a buffer chamber which receives a buffer solution; a bead chamber which receives a bead solution containing the beads; a mixing chamber containing which is fluid connected to the sample chamber, the buffer chamber, and the bead chamber through the channel; which receives a solution containing the second probe; which comprises an inlet to receive a fluid and an outlet to discharge the fluid, the outlet being disposed with a greater distance from the rotation center of the body of revolution than the inlet, and the outlet being provided with a valve to control a flow of the fluid discharged from the mixing chamber; and in which the sample and the beads are brought into contact with each other to produce a bead-target molecule-second probe complex, if the fluid biological sample contains the target molecule; and separates the bead-target molecule-second probe complex; a waste chamber which is fluid connected to the outlet of the mixing chamber through a channel, the waste chamber receiving the fluid discharged from the mixing chamber by changes of phases of a valve; and an optical signal emission chamber connected to the outlet of the mixing chamber through a channel, in which a substrate solution is brought into contact with the bead-target molecule-second probe complex to generate an optical signal.

Here, wherein the guide rail may provide a path which connects positions respectively corresponding to the bead chamber, the mixing chamber, and the optical signal expression chamber.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The above and other features and advantages of the present invention will become more apparent by describing in detail exemplary embodiments thereof with reference to the attached drawings in which.

DETAILED DESCRIPTION OF THE INVENTION

Hereinafter, the present invention will be described more fully with reference to the accompanying drawings, in which exemplary embodiments of the invention are shown.

Figure 1:
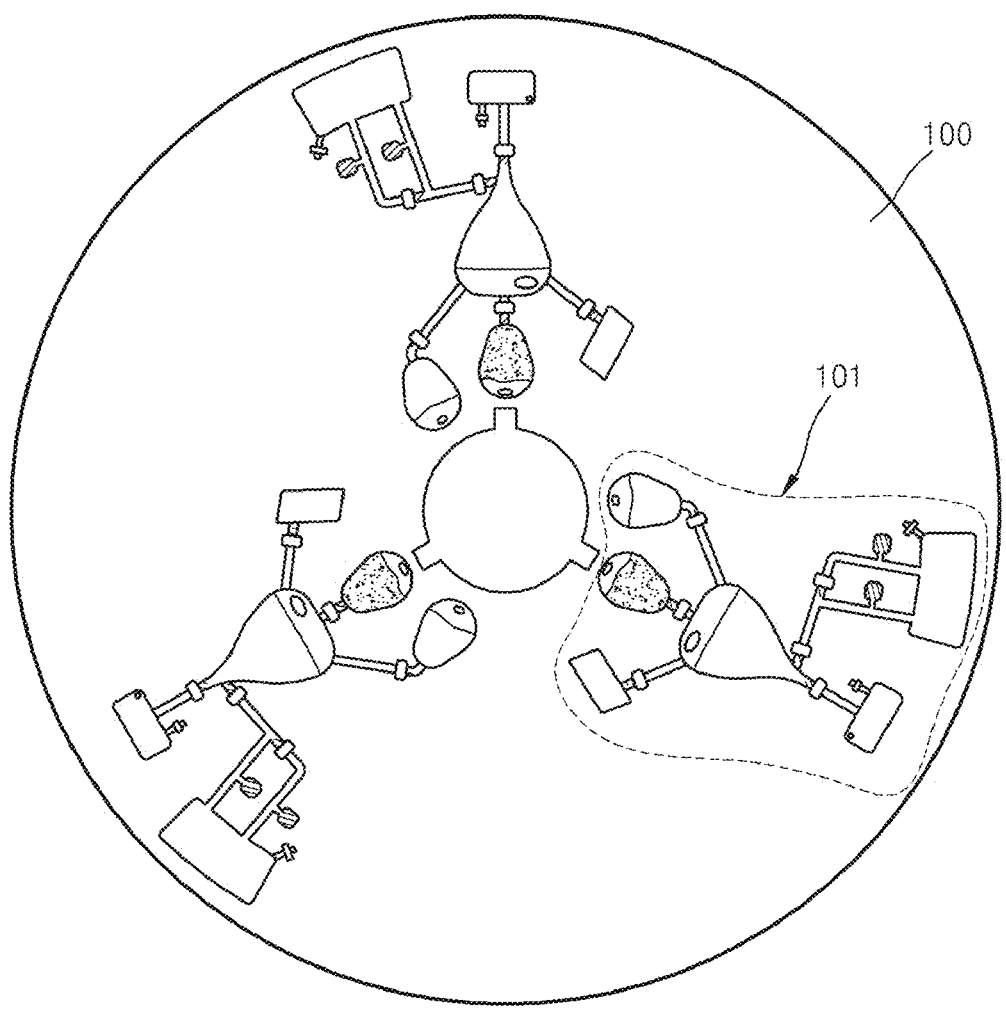
FIG. 1 is a plan view schematically illustrating a microfluidic device according to an embodiment of the present invention.

FIG. 1 is a plan view schematically illustrating a microfluidic device according to an embodiment of the present invention. Referring to FIG. 1, the microfluidic device includes a body of revolution 100 and one or more microfluidic structures 101 disposed on the body of revolution 100. According to the current embodiment of the present invention, the body of revolution 100 may be a disk-shaped platform. The platform can be easily manufactured and formed of plastic materials such as an acryl and PDMS and the surface of the platform is deactivated. However, the materials are not limited to the examples above and may be any materials having chemical and biological stability (i.e., inactivity), optical transparency, and mechanical processability. The body of revolution 100 may have a hole at the center thereof. Since the hole receives a rotation operating unit (not illustrated) and a spindle (not illustrated), the body of revolution 100 can rotate. Thus, the center of the body of revolution 100 acts as a rotational axis.

The body of revolution 100 may include one or more microfluidic structures 101 therein. The body of revolution 100 may be formed of a pair of a first disk and a second disk. Or, the body of revolution 100 may be formed of a first disk, a second disk, and a lid disk. These disks are adhered to each other at, for example their circumferences by known methods. Such microfluidic structures 101 may be provided by a three-dimensional pattern formed on any one or both of the first and the second disks. The lid disk may have a plurality of through holes which serve as an inlet and/or outlet. A double-sided bonding layer may be interposed between the two disks. However, the structure of the microfluidic structures 101 is not limited thereto. When two or more microfluidic structures 101 are included in the body of revolution 100, a target molecule such as a protein, polypeptide, carbohydrate, or the like can be detected from various samples, for example, blood specimens from a number of people at the same time. In addition, different target molecules can be detected from one sample in respective individual microfluidic structure 101.

Figure 2:
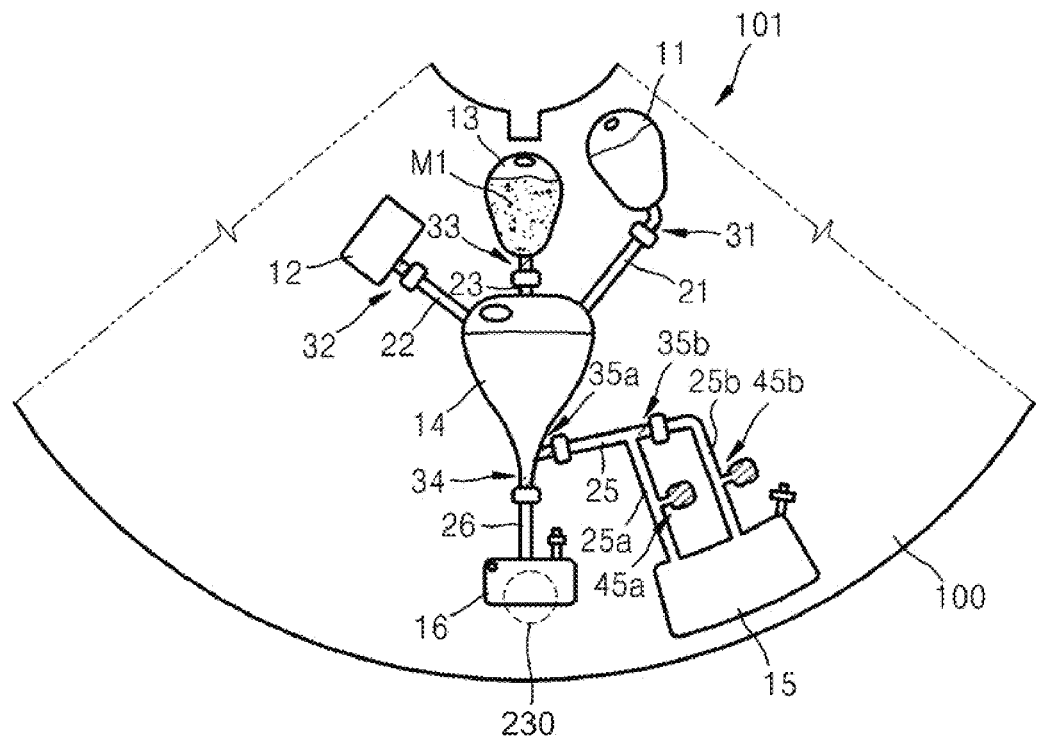
FIG. 2 is an enlarged view illustrating a part of the microfluidic device of FIG. 1, according to an embodiment of the present invention.

FIG. 2 is an enlarged view illustrating one section of the microfluidic device of FIG. 1, according to an embodiment of the present invention. The microfluidic structure 101 schematically illustrated in FIG. 1 is described below with respect to an exemplary usage. The top part and lower part of the section of the body of revolution 100 of FIG. 1, as depicted on the sheet of drawing, are each a center and a circumference part of the body of revolution 100, respectively. The microfluidic structure 101 according to the current embodiment of the present invention includes a sample chamber 11, a buffer chamber 12, and a bead chamber 13, wherein the sample chamber 11 receives a fluid sample, the buffer chamber 12 receives a buffer solution, and the bead chamber 13 includes a plurality of particles such as beads. Each of the sample chamber 11, the buffer chamber 12, and the bead chamber 13 include an inlet through which samples, a buffer solution, and a bead solution can be introduced by, for example injection. The target molecule which is to be separated from the fluid biological samples may be a protein, polypeptide, or carbohydrate, etc. In the present specification, a protein is exemplified as a target molecule to be separated, but it should be noted that the present invention may be applied to the separation of different molecules of interest using, for example, different capture probes, buffer solutions, and the like.

The distance from a center of the rotation body 100 to the mixing chamber 14 is greater than the distances from the center to the sample chamber 11, the buffer chamber 12, and the bead chamber 13. The mixing chamber 14 is fluid connected to the sample chamber 11, the buffer chamber 12, and the bead chamber 13 through channels 21, 22, and 23, respectively, wherein the channels 21, 22, and 23 are fluid transfer passages. Valves 31, 32, and 33 which control fluid flow are disposed in the channels 21, 22, and 23, respectively. The three valves 31, 32, and 33 may be opening valves which are closed normally and open when desired. The mixing chamber 14 has an outlet at a location farthest from the center (or rotation axis) of the body of revolution 100, wherein the outlet includes a valve 34 (hereinafter, referred to as outlet valve). The mixing chamber 14 may have a shape with different cross-sectional dimensions along the radial direction of the rotation body 100. For example, it has a smaller dimension near its outlet portion, i.e., near the circumference of the body of revolution 100 than its center portion, as depicted in FIG. 2. Also, the narrower outlet area can have an extended length. In this case, a portion of the inside of the outlet valve 34 can be formed as a channel. Meanwhile, the mixing chamber 14 may contain a detection probe solution introduced in advance. In addition, a fluid sample, a buffer solution, and a beads (M1) solution may be introduced to the mixing chamber 14 from the sample chamber 11, the buffer chamber 12, and the bead chamber 13, respectively.

A waste chamber 15 is disposed far away from the rotation axis of the body of revolution 100 than the mixing chamber 14. The waste chamber 15 can be connected to the outlet area of the mixing chamber 14, through a channel 25. In this case, there should be enough space between the place of the mixing chamber 14 to which the channel 25 is connected and the outlet valve 34 so that the beads M1 are collected in the bottom area (i.e., where there is an outlet of the mixing chamber 14).

The fluids can flow into the waste chamber 15 from the mixing chamber 14 at least two times. First, sample residue obtained after a reaction with the beads M1 flows into the waste chamber 15 and then a buffer solution which rinses the beads M1 flows into the waste chamber 15. Therefore, the channel 25 may include a valve which can open and close at least two times. When a single use valve which can either open or close a channel once is used, the channel 25 may include at least two branch channels 25a and 25b through which the fluids flow into the waste chamber 15 from the mixing chamber 14 to be used one at a time. In addition, the two branch channels 25a and 25b may be closed after each channel transfers the fluids once. Accordingly, opening valves 35a and 35b and closing valves 45a and 45b can be disposed in the branch channels 25a and 25b.

Moreover, an optical signal expression chamber 16 is disposed further away from the center of the body of revolution 100 than the outlet of the mixing chamber 14. The optical signal expression chamber 16 is connected with the outlet valve 34 disposed in the mixing chamber 14 through a channel 26. The optical signal expression chamber 16 may contain a substrate solution introduced in advance, wherein the substrate binds to a target protein captured by the beads M1, and then the substrate is allowed to react with an optical signal expression material of the detection probe solution flowing into the optical signal expression chamber 16 and to express an optical signal. The substrate solution may include a substrate and an enzyme which are needed to generate optical signal after reacting with the optical signal expression material of the detection probe. In addition, a magnetic material which generates a magnetic field, for example, a magnet 230 may be disposed near the optical signal expression chamber 16. When the beads M1 are of magnetic materials, the magnet 230 attracts the magnetic beads, which then are collected in the mixing chamber 14. Beads M1 will be explained in more detail hereinafter.

Meanwhile, the magnet 230 may move to various positions along a radial direction of the body of revolution 100 and supports a position control of the magnetic beads. For example, the magnet 230 moves the magnetic beads, which are separated and collected using centrifugal force, at the outlet of the bead chamber 13 or the mixing chamber 14 to the center of each chamber (bead chamber 13 or the mixing chamber 14) so that the magnetic beads can be easily dispersed in a fluid contained in the chambers.

In order for the beads M1 to capture a target biological material (including an antigen on the surface of a pathogen) from biomaterial samples such as whole blood, saliva, and urine, the beads M1 have probes that capture the target material through a specific binding to the target material. For example, the capture probes may be antibodies that are coupled to the surfaces of the beads M1. The antibodies have a unique affinity for a specific target material, for example, an antigen protein on the surface of certain cells and viruses and thus are useful when detecting cells and viruses of a significantly low concentration. The magnetic beads coupled with antibodies which can specifically bind to antigens are commercially available from, for example Invitrogen and Qiagen. Examples of the magnetic beads may be DYNABEADS® Genomic DNA Blood (Invitrogen), DYNABEADS® anti-*E. coli* O157 (Invitrogen), CELLECTION™ Biotin Binder Kit (Invitrogen), and MAGATTRACT Virus Min M48 Kit (Qiagen). Diphtheria toxin, *Enterococcus faecium, Helicobacter pylori*, Hepatitis B virus (HBV), Hepatitis C virus (HCV), Human immunodeficiency virus (HIV), Influenza A, Influenza B, *Listeria, Mycoplasma pneumoniae, Pseudomonas* sp., Rubella virus, and Rotavirus can be separated using magnetic beads combined with specific antibodies. Alternatively, desired magnetic beads which has desired probes may be fabricated by a method explained in commonly owned co-pending application Ser. Nos. 11/752,321 and 11/839,023, contents of which are incorporated herein in their entirety by reference.

The size of the beads M1 may be 50 nm to 10 mm, for example, 1 μm~50 μm for chamber-to-chamber moving beads, and 150 μm to 5 mm for one-chamber-confined beads. The beads M1 may be a mixture of two or more types of beads having different sizes. In other words, the beads M1 may have uniform sizes or various sizes.

The beads M1 may be formed of any magnetized materials. In particular, the beads M1 may include one or more materials selected from the group of ferromagnetic metals consisting of Fe, Ni, and Cr and oxides thereof.

The beads M1 may be formed of a non-magnetic material. For example, the non-magnetic material may be PS (polystyrene) PMMA (polymethylmethacrylate).

In the detection probes including the optical signal expression material, materials for detection probes used in a conventional enzyme-linked immunosorbent assay (ELISA) can be used. For example, when a primary antibody is adhered to the surfaces of the beads M1 as a capture probe for detecting a target antigen or an antigen on a target material, a second antibody in which a marker such as horseradish peroxidase (HRP) is combined can be employed as the detection probes. In this case, the optical signal emit chamber 16 may include a substrate solution including a substrate and an enzyme. The substrate and the enzyme produce changes in colors due to a reaction with HRP. Even though a HRP is explained above with respect to an optical signal emitter, other optical signal emitting substances, which are known in the art, may be used. Also, instead of optical signal emitting substances, other types of signal emitter may be used for the same purposes.

Figure 3:
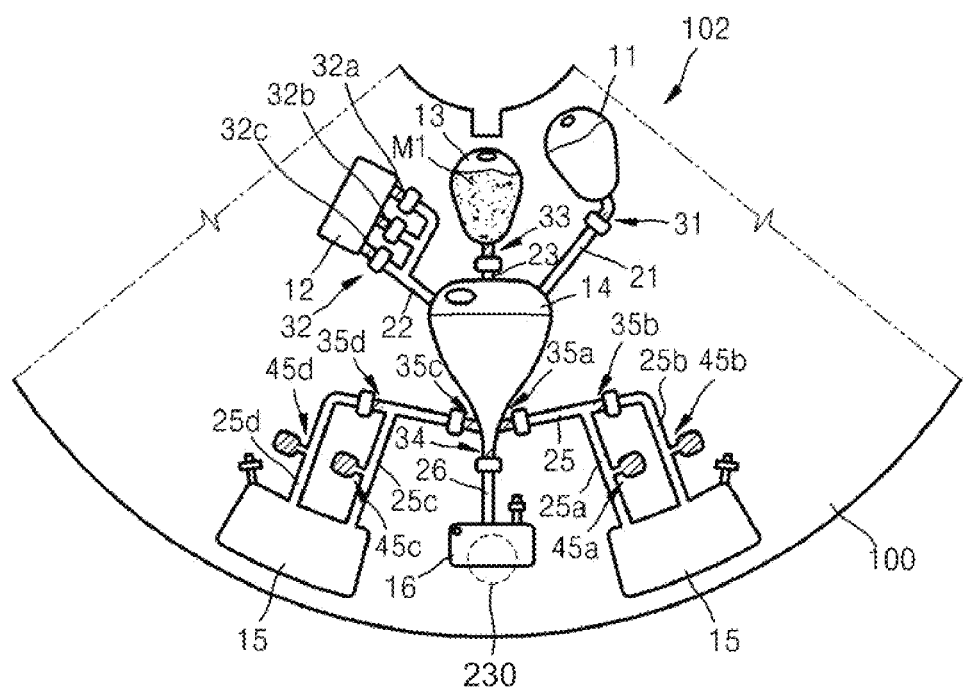
FIG. 3 is a plan view schematically illustrating a microfluidic device according to another embodiment of the present invention.

FIG. 3 is a plan view schematically illustrating a microfluidic device according to another embodiment of the present invention. The microfluidic device according to the current embodiment of the present invention includes a microfluidic structure 102 which is similar to the microfluidic structure 101 of FIG. 2 according to the previous embodiment of the present invention, except the structure of the channel 22 which fluid connects the mixing chamber and the buffer chamber 12 and the addition of a second waster chamber 15. The buffer chamber 12 of the microfluidic structure 102 is formed here larger than that of the microfluidic structure 101. In addition, the channel 22 connecting the buffer chamber 12 and the mixing chamber 14 is branched off in a number of channels and thus each branched channel can be connected with positions corresponding to various levels of fluid in the buffer chamber 12. Here, each of the branched channels may include valves 32a, 32b, and 32c, wherein the valves 32a, 32b, and 32c may be opening valves which can be operated individually and independently. In this embodiment, the microfluidic structure 101 has a second waste chamber 15. Channels 25c and 25d and valves 35c and 35d can be added, wherein the channels 25c and 25d and valves 35c and 35d discharge the fluids from the mixing chamber 14 to the second waste chamber 15 as fluid flows into the mixing chamber, and then are closed. Accordingly, a small amount of a buffer solution contained in the buffer chamber 12 is provided to the mixing chamber 14 to wash the beads M1, and remaining of the buffer solution separated from the beads M1 is discharged into the waste chamber 15 each time.

Figure 4:
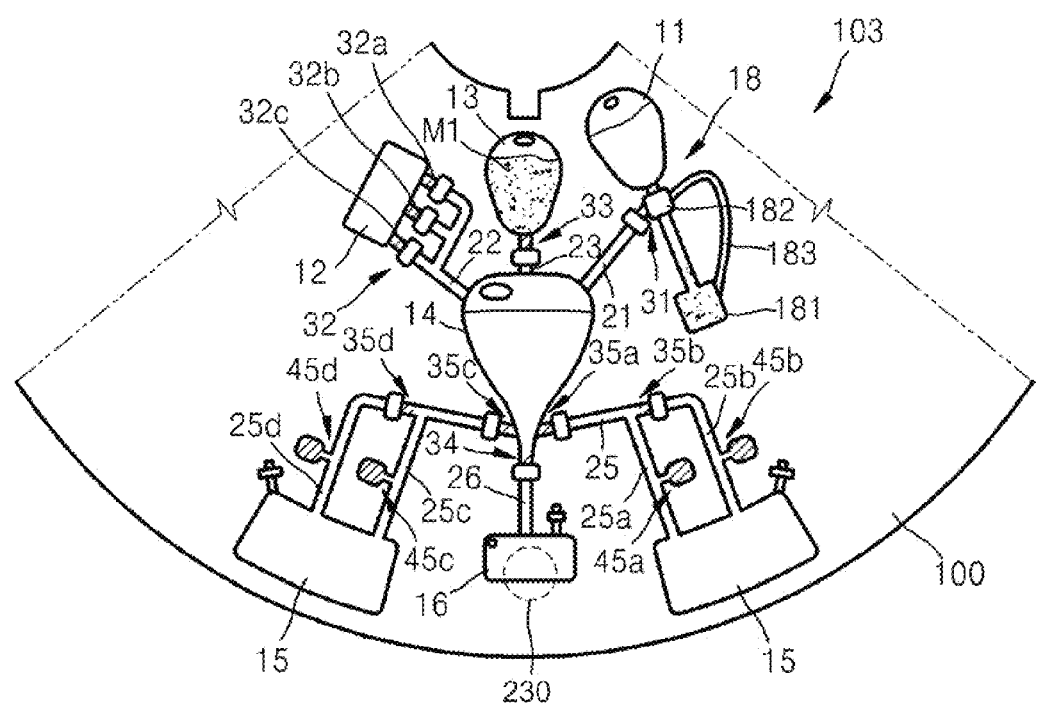
FIG. 4 is a plan view schematically illustrating a microfluidic device according to another embodiment of the present invention.

FIG. 4 is a plan view schematically illustrating a microfluidic device according to another embodiment of the present invention. The microfluidic device according to the current embodiment of the present invention includes a microfluidic structure 103 which is similar to the microfluidic structure 102 of FIG. 3 according to the previous embodiment of the present invention. The differences between the microfluidic structure 103 and the microfluidic structure 102 are as follows. The microfluidic device 103 further includes a centrifuging unit 18 which is disposed between the outlet of the sample chamber 11 and the mixing chamber 14. The centrifuging unit 18 includes a supernatant channel 182 and a precipitate collecting unit 181, and a portion of the supernatant channel 182 is fluid connected with the mixing chamber 14 through the valve 31 and the channel 21, wherein the supernatant channel 182 is extended from the outlet of the sample chamber 11 towards the circumference of the body of revolution 100 and the precipitate collecting unit 181 having expanded width is disposed at a distance toward the circumference of the body of revolution 100. The supernatant channel 182 and the precipitate collecting unit 181 are fluid connected through a channel. Here, the precipitate collecting unit 181 and the supernatant channel 182 can also be connected to each other through a bypass channel 183. The bypass channel 183 acts as an exhaust pipe of the precipitate collecting unit 181 and supports the sample chamber 11 in providing a fixed amount of the sample fluid into the mixing chamber 14, even if an excessive amount of the sample fluid is introduced into the sample chamber 11.

A detailed description of an operation of the centrifuging unit 18 is as follows. When whole blood is introduced into the sample chamber 11 and then the body of revolution 100 is rotated, blood cells (e.g., red blood cells, white blood cells, platelets, etc) are collected in the precipitate collecting unit 181 and serum is received in the supernatant channel 182. In this case, when the valve 31 of the channel 21, which fluid connects the supernatant channel 182 to the mixing chamber 14, is opened, serum in the supernatant channel 182 flows into the mixing chamber 14 by centrifugal force. That is, the serum in the supernatant channel 182 is positioned closer to the center of the body of revolution 100 than the channel 21 and transferred to the mixing chamber 14 when the valve 31 is open. Accordingly, in the microfluidic device 103 according to the current embodiment of the present invention, blood cells which may interfere with an accurate detection of a target material can be removed from the sample fluid beforehand.

Figure 5:
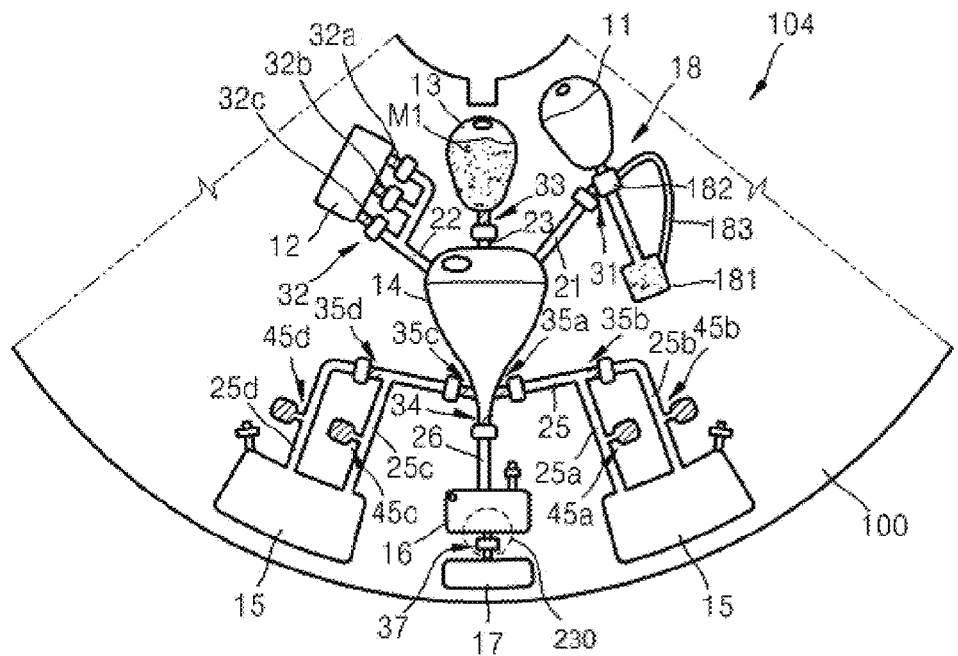
FIG. 5 is a plan view schematically illustrating a microfluidic device according to another embodiment of the present invention.

FIG. 5 is a plan view schematically illustrating a microfluidic device according to another embodiment of the present invention. The microfluidic device according to the current embodiment of the present invention includes a microfluidic structure 104 which is similar to the microfluidic structure 103 of FIG. 4 according to the previous embodiment of the present invention. However, the differences between the microfluidic structure 104 and the microfluidic structure 103 are as follows. The microfluidic structure 104 may further include a stopping chamber 17 connected to the optical signal expression chamber 16 by a valve 37 which is disposed between the stopping chamber 17 and the optical signal expression chamber 16. The stopping chamber 17 includes the substrate solution included in the optical signal expression chamber 16 and a stopping solution which stops reaction of the optical signal expression material of the detection probe. Thanks to the action of the stopping solution, a reaction which generates optical signal emission is stopped when the valve 37 is opened and a mixed fluid of the substrate solution and the beads M1, which have surface adhesion materials flows into the stopping chamber 17. As such, the strength of the optical signal can be maintained constantly. Accordingly, the time to progress a reaction of optical signal emission can be uniformly controlled. Thus, during detecting an optical signal using a light detecting unit (70, refer to FIG. 10), regardless of the point of time of measuring the signal, an objective comparison of the strengths of the detected optical signal is possible.

Although the above embodiments illustrate that the mixing chamber 14 receives the bead solution supplied from the bead chamber 13, the bead solution may be directly injected into the mixing chamber 14. Further, if the bead solution is received in the mixing chamber 14, the microfluidic structures 101, 102, 103, and 104 may not be provided with the bead chamber 13.

Differing from the description in the above embodiments, the beads M1 may not move to the optical signal expression chamber 16. For this purpose, non-magnetic beads having a large size so as not to pass through the channel 26 may be used. The substrate solution may be directly injected into the mixing chamber 14 so as to react with the second probe binding to the surfaces of the non-magnetic beads together with the target protein. Further, if the substrate solution reacts with the second probe in the mixing chamber 14, the termination solution may be directly injected into the mixing chamber 14 so as to stop reaction to express an optical signal.

The valves 31, 32a through 32c, 33, 34, 35a through 35d, and 45a through 45d described in the above embodiments can be selected from the group consisting of a capillary valve, a hydrophobic valve, a mechanical valve, and a phase-change valve. The phase-change valve may include a valve plug including heat generating particles and phase-change materials, and the heat generating particles absorbing an energy, for example electromagnetic wave and generate heat to melt the phase-change materials. The phase-change valve control the flow of fluid passing through the channels according to positions of the valve plug in the channels.

Here, the phase-change valve may include an opening valve, wherein the opening valve is disposed for the valve plug to close the channel at an initial stage and moves to a space which is adjacent to the initial position of the valve plug after the valve plug is melted by heat, to open the channel. In addition, the phase-change valve may also include a closing valve which is disposed in a valve chamber connecting with the channel for the valve plug to open the channel at an initial stage and to flow into the channel after the valve plug is melted and expanded by heat, to close the channel. Hereinafter, the phase-change valve which can be employed in the microfluidic device according to the current embodiment of the present invention described above will be described more fully. Examples of valve units comprising phase-change valve, which may be implemented into the microfluidic systems according to embodiments of the present invention, other modifications and changes are described, for example, in a commonly owned, co-pending application Ser. No. 11/770,762, disclosure of which is incorporated by reference.

Figure 6:
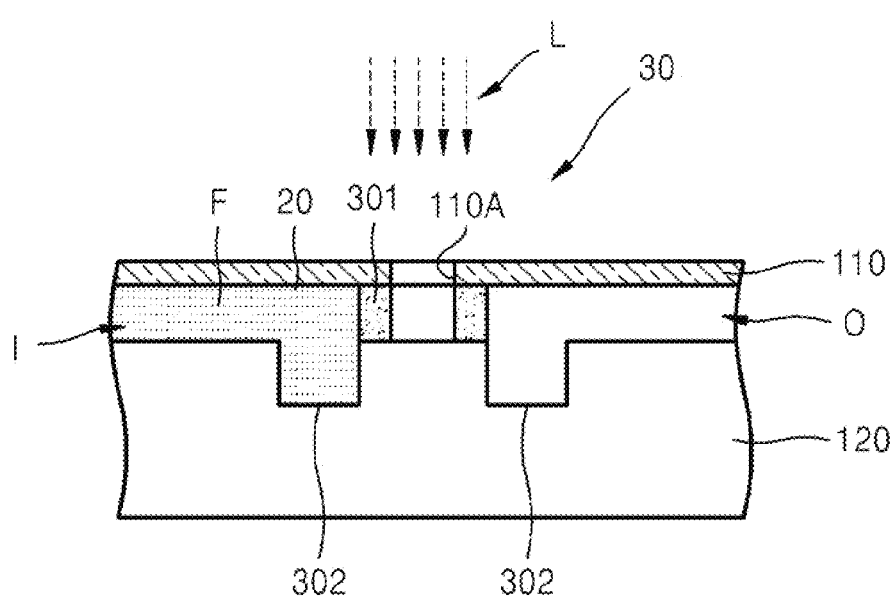
FIG. 6 is a cross-sectional view of an opening valve which controls fluid flow in a microfluidic device according to an embodiment of the present invention.

FIG. 6 is a cross-sectional view of an exemplary opening valve which may be used to control the fluid flow in a microfluidic device according to an embodiment of the present invention. The opening valve 30 which is an example of the phase-change valve (corresponding to the valves 31, 32, 33, 34, 35a through 35d, and 37 of FIGS. 2 through 5) includes a valve plug 301 in which heat generating particles are dispersed in phase-change materials, wherein the phase-change materials are at a low viscosity stage (e.g., solid) at ambient temperature. In a lower part and an upper part of a channel 20 which is adjacent to the initial position of the valve plug 301, wherein the valve plug 301 is in a solid state, a pair of channel expansion units 302 providing an available space prepared by expanding the width or the depth of the channel expansion unit 302 are disposed.

The valve plug 301, which is introduced through a through hole 110A when it is in a melted state and then solidified, prevents flow of fluids F from an inlet I by blocking the channel 20 at ambient temperature.

When the valve plug 301 is melted at high temperature, it moves to the adjacent channel expansion units 302 and thus is solidified while the channel 20 is opened.

In order to heat the valve plug 301, an external energy source (not illustrated) is disposed outside the microfluidic device, and the external energy source can radiate an electromagnetic wave to a region including the initial position of the valve plug 301. Here, the external energy source may be laser light source irradiating a laser beam L, visible rays, a light emitting diode irradiating infrared rays, or a xenon lamp. In particular, in the case of a laser light source, at least one laser diode can be included. The external energy source can be selected according to a wavelength of the electromagnetic wave, which can be absorbed by heat generating particles included in the valve plug 301.

The channel 20 can be provided by a three-dimensional pattern formed on an inner part of a first disk 110 or an inner part of a second disk 120, both form together the body of revolution 100. The first disk 110 transmits electromagnetic waves irradiated from the external energy source (not illustrated) to be incident onto the valve plug 301. In addition, the first disk 110 may be formed of optically transparent material in order to observe the fluid F from the outside. For example, glass or transparent plastic have excellent optical transparency and low manufacturing costs.

The size of the heat generating particles dispersed in the valve plug 301 may be of the order of thousands of μm, and thus, can freely move in the channel 20. When an electromagnetic wave is irradiated, the temperature of the heat generating particles is rapidly increased by the energy so as to generate heat, and the heat generating particles are uniformly dispersed in phase changing materials such as wax. In order for the heat generating particles to be dispersed uniformly in a phase changing material, the heat generating particles may have structures including a core having a metallic component and a hydrophobic shell. For example, the heat generating particles may include a core formed of Fe, which is a ferromagnetic material, and a shell formed of a plurality of surfactants which are bonded to Fe to surround the Fe core. In general, the heat generating particles are provided in a dispersed form on a carrier oil. In order for the heat generating particles having hydrophobic surfaces to be dispersed uniformly, the carrier oil may also be hydrophobic. The valve plug 301 can be manufactured by mixing the carrier oil containing the heat generating particles dispersed therein with the phase-change materials. The form of the heat generating particles is not limited to the examples above and may be polymer beads, quantum dots, or magnetic beads.

The valve plug 301 may be formed of a phase-change material such as wax. When the radiation energy absorbed by the heat generating particles is dissipated in the form of heat energy, the wax is melted so as to have fluidity and thus a form of the valve plug 301 is broken down to open the flow channel of the fluids F. The wax forming the valve plug 301 may have an adequate melting point. When the melting point of the wax is too high, time required for the wax to be melted after laser irradiation is started is increased and thus an opening time is hardly controlled. When the melting point of the wax is too low, the fluids F can be leaked, since the wax is partially melted while laser is not irradiated. Examples of the wax may be paraffin wax, microcrystalline wax, synthetic wax, or natural wax.

Meanwhile, the phase-change material may be gel or a thermoplastic resin. Example of the gel may include polyacrylamide, polyacrylates, polymethacrylates, and polyvinylamides. In addition, the thermoplastic resin may be COC (cyclic olefin copolymer), PMMA (polymethylmethacrylate), PC (polycarbonate), PS (polystyrene), POM (polyoxymethylene), PFA (perfluoralkoxy), PVC (polyvinylchloride), PP (polypropylene), PET (polyethylene terephthalate), PEEK (polyetheretherketone), PA (polyamide), PSU (polysulfone), or PVDF (polyvinylidene fluoride).

Figure 7:
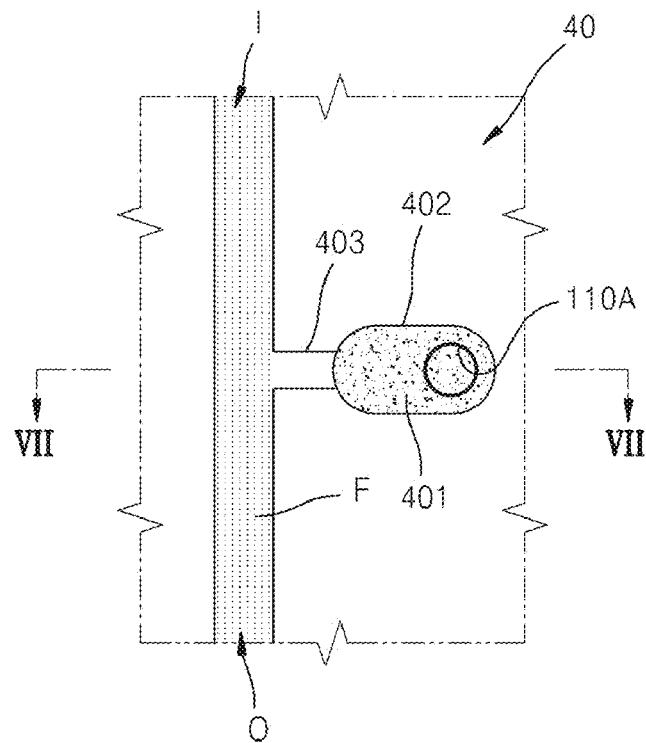
FIG. 7 is a plan view of a closing valve which controls fluid flow in a microfluidic device according to an embodiment of the present invention.
Figure 8:
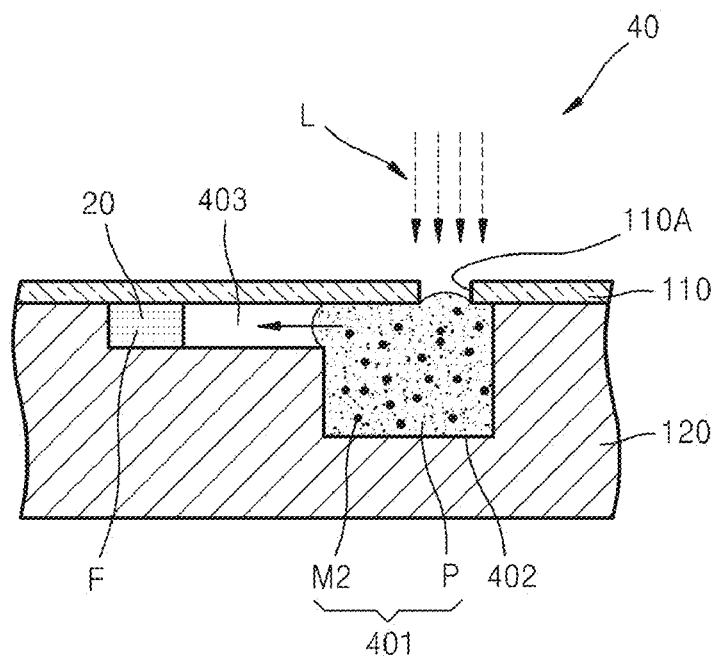
FIG. 8 is a cross-sectional view of the closing valve of FIG. 7 according to an embodiment of the present invention.

FIG. 7 is a plan view of a closing valve which controls fluid flow in a microfluidic device according to an embodiment of the present invention and FIG. 8 is a cross-sectional view of the closing valve of FIG. 7 according to an embodiment of the present invention.

The closing valve 40 (corresponding to the valves 45a through 45d of FIGS. 2 through 5) which is another example of a phase-change valve, includes a channel 20, a valve chamber 402, and a valve plug 401. Here, the channel 20 includes an inlet I and an outlet O and the valve chamber 402 is connected to the center of the channel 20. In addition, the valve plug 401 in the valve chamber 402 in a solid-form at ambient temperature at an initial stage flows into the channel 20 after the valve plug 401 is melted and expanded by heating and is solidified again to block fluids F flowing through the channel 20.

Similar to the above-described opening valve 30, the structure of the closing valve 40 can be provided by a three-dimensional pattern formed on an inner part of a first disk 110 or an inner part of a second disk 120, both consisting of the body of revolution 100. The first disk 110 may have a through hole 110A which corresponds to the valve chamber 402 in order for electromagnetic waves (for example, a laser beam) to be easily incident onto the valve plug 401.

Phase-change materials P and heat generating particles M2, which form the valve plug 401, are the same as those of the opening valve 30 described above. In addition, the external energy source (not illustrated) which provides an electromagnetic wave L to the valve plug 401 is as described above.

When a laser beam is irradiated to the valve plug 401 including the phase-change materials P and the heat generating particles M2, both of which constitute a dispersing medium, the heat generating particles M2 absorb radiation energy to heat the phase-change materials P. Accordingly, the volume of the valve plug 401 is expanded while the valve plug 401 is melted, and the valve plug 401 flows into the channel 20 through a channel 403 connected with the channel 20. The valve plug 401 which is cooled down after contacting the fluids F in the channel 20, blocks the fluids F flowing through the channel 20.

Figure 9:
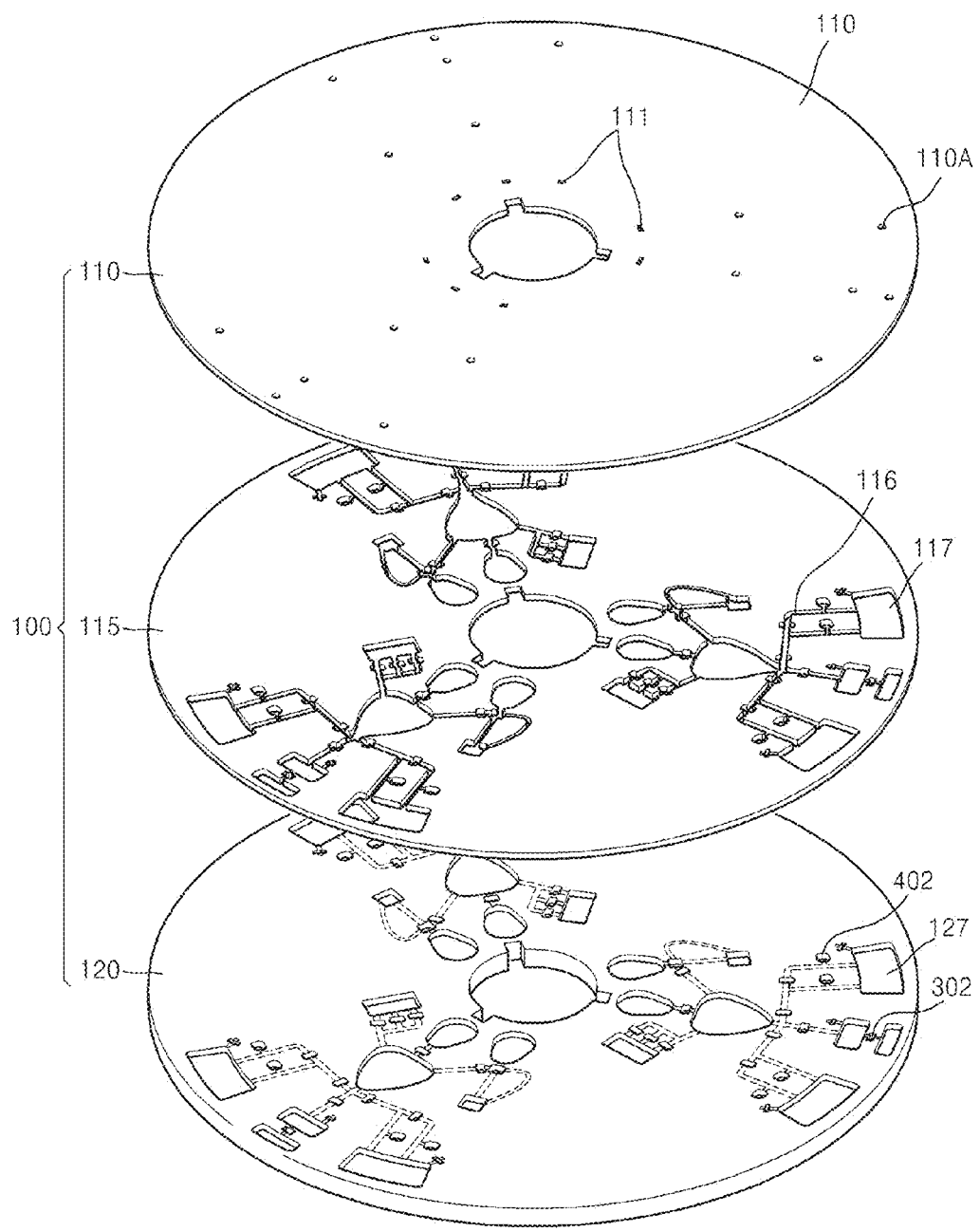
FIG. 9 is a detailed perspective view of the microfluidic device of FIG. 5 according to an embodiment of the present invention.

FIG. 9 is a detailed perspective view of the microfluidic device of FIG. 5 according to an embodiment of the present invention. The microfluidic device including the microfluidic structure 104 according to the current embodiment of the present invention includes the first disk 110, the second disk 120, and a double-sided adhesive sheet 115 to adhere the first disk 110 and the second disk 120 to each other. The first disk 110 and the second disk 120 may be formed of a transparent plastic substrate, for example, a polycarbonate substrate.

The first disk 110 includes a number of inlets 111 which penetrate the upper and lower surface of the first disk 110 and a number of through holes 110A. The inlets 111 may be disposed to correspond to the sample chamber, the bead chamber, and the buffer chamber and the through holes may be disposed to correspond to the initial position of the valve plug in a number of phase-change valves.

The second disk 120 includes a number of grooves 127 which have a certain depth so as to form a chamber structure when the second disk 120 is bonded to the first disk 110. The depth may be, for example, 3 mm. In addition, the second disk 120 may further include intaglio structures including the channel expansion units 302 and valve chambers 402.

The double-sided adhesive sheet 115 may be prepared with a double-sided adhesive tape that is commonly used, for example, FLEXMOUNT™ DFM 200 Clear V-95150 POLY H-9 V-96 4, FLEXcon Inc., MA, USA. The double-sided adhesive sheet 115 includes a number of chamber outlines 117 corresponding to the grooves 127 and a number of channel outlines 116 corresponding to the channels described in FIG. 4. The channel outlines 116 may have the depth of 1 mm. Since the thickness of the double-sided adhesive tape that is commonly used is 100 µm, the depth of the channel formed by the first disk 110, the second disk 120, and the double-sided adhesive sheet 115 is 100 µm. The depth of the channel can be easily changed according to the thickness of the double-sided adhesive sheet 115.

The inlets 111, through holes 110A, grooves 127, and channel outlets 116 can be formed on each of the first disk 110, the second disk 120, and the double-sided adhesive sheet 115 by computer numerical control (CNC) machining The detailed structure and standard of the microfluidic device is only an example and is not limited thereto. For example, the first disk 110 and the second disk 120 can be adhered to each other by using various plastic bonding methods such as thermal bonding, low temperature bonding, chemical bonding, or ultrasonic bonding, instead of using the double-sided adhesive sheets 115. The standard of the channels and chambers can become larger or smaller according to the size of the microfluidic device and an amount of samples to be processed. Meanwhile, when bonding means other than the double-sided adhesive sheets 115 are used, the channel can be formed in a trench form on the upper surface of the second disk 120. In addition, in the embodiments described above, the microfluidic structure is prepared on one layer, however, can be formed on a plurality of layers, each layer having the microfluidic structure including channels and chambers.

Figure 10:
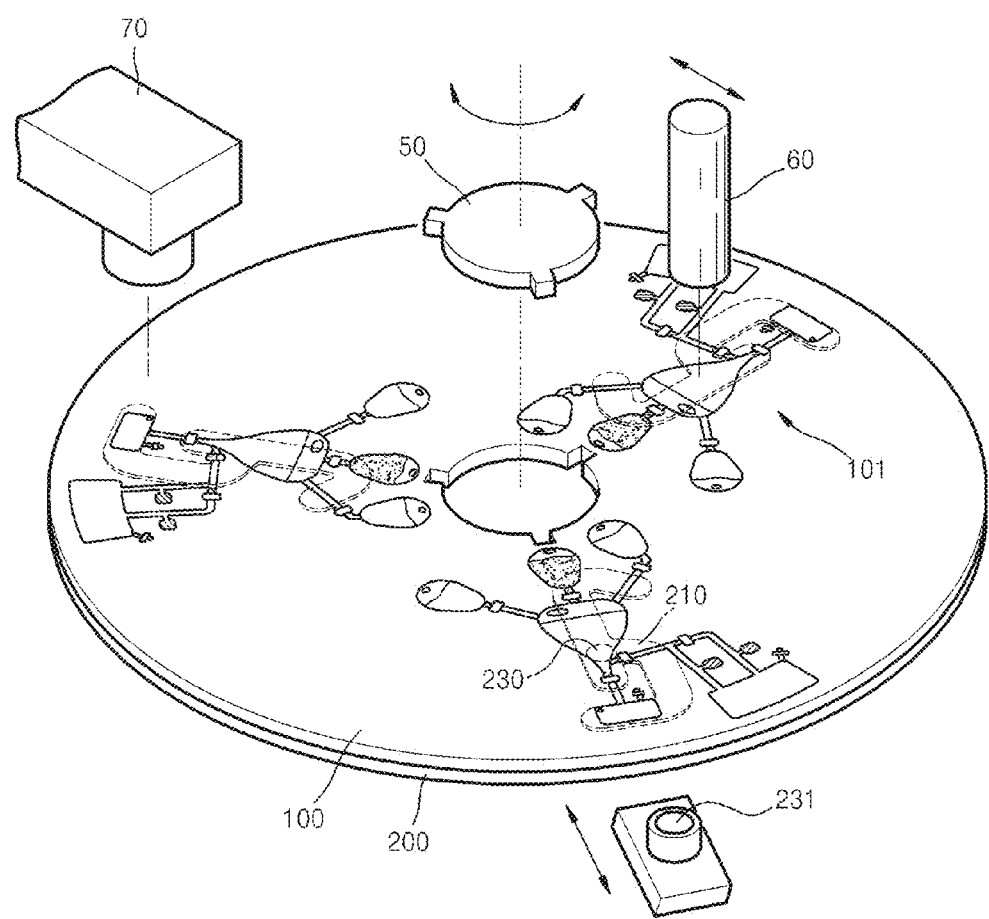
FIG. 10 is a perspective view schematically illustrating a microfluidic system according to an embodiment of the present invention.

FIG. 10 is a perspective view schematically illustrating a microfluidic system according to an embodiment of the present invention. The microfluidic system according to the current embodiment of the present invention which includes at least one microfluidic structure 101 prepared on the body of revolution 100 includes any of the microfluidic devices according to the previous embodiments, a rotation operating unit 50 which rotates the body of revolution 100, and a light detecting unit 70 which can optically detect the captured biomaterial of interest, which is obtained using the microfluidic device. In addition, the microfluidic system may further include an external energy source 60 which can irradiate an electromagnetic wave onto selected regions formed on the body of revolution 100. The microfluidic system, which will be described in more detail, and other modifications, which may be used in the present application are described in commonly owned, co-pending application Ser. No. 11/847,623, filed Aug. 30, 2007, content of which is incorporated herein in its entirety by reference.

The external energy source 60 can be used to maintain a temperature of chambers adequately in which reactions occur in the microfluidic device according to an embodiment of the present invention, for example, the mixing chamber 14 and the optical signal expression chamber 16. Here, laser light source, a light emitting diode, or a xenon lamp can be employed as described above. In addition, when a phase-change valve including heat generating particles M2 such as magnetic beads is used in the microfluidic device, the external energy source 60 can be used to operate the phase-change valve.

The microfluidic system may include an external energy source adjusting means (not illustrated) which adjusts position or direction of the external energy source 60 and concentrates electromagnetic waves irradiated from the external energy source 60 in a desired region on the body of revolution 100, more specifically, a region corresponding to an element selected from a number of phase-change valves 31 and etc., the mixing chamber 14, and the optical signal emission chamber 16 included in the microfluidic device.

Meanwhile, according to the current embodiment of the present invention, the microfluidic system may further include a magnet position control device which can move the magnet 230 to positions corresponding to various parts of the microfluidic device. The magnet position control device moves the magnetic beads in the microfluidic device or traps the magnetic beads to a specific position. Some elements of the magnet position control device can be formed as one body on the bottom surface of the lower disk 120 in the microfluidic device as illustrated in FIG. 9. For example, the magnet position control device may include a revolution plate 200 that is bonded with the body of revolution 100 at the bottom of the microfluidic device and an external magnet 231 disposed outside of the revolution plate 200. The revolution plate 200 includes a guide rail 210 and the magnet 230 moves along the guide rail 210. The shape of the guide rail 210 can be changed according to an arrangement of the chambers and the channels in the microfluidic device and the movement order of fluids including the magnetic beads. Thus, the guide rail 210 may be a path which can connect various positions having each different distance from the rotational axis of the revolution plate 200 and move the magnet 230.

The external magnet 231 can be disposed to be fixed to a specific position or to be temporarily fixed to a desired position while moving along a radial direction of the revolution plate 200. The external magnet 231 influences magnetic force to the extent that the position of the magnet 230 in the guide rail 210 is moved and should not influence magnetic force to the extent that the magnetic beads in the microfluidic device are moved.

When the microfluidic device and the revolution plate 200 are simultaneously rotated, centrifugal force of an outside direction of the radius and magnetic force (gravitation or repulsive force) are influenced to the magnet 230 in the guide rail 210 and thus the magnet 230 moves to a position where both forces are balanced. In addition, when the revolution plate 200 starts rotating, the magnet 230 can move in a circumferential direction due to inertial force influence to the magnet 230. A permanent magnet can be employed as the magnet 230 and the external magnet 231. An example of the permanent magnet may include a neodymium magnet (Nd—Fe—B).

According to the current embodiment of the present invention, the guide rail 210 provides a path which connects the positions corresponding to the bead chamber 13, the outlet and the center of the mixing chamber 14, and the optical signal emission chamber 16. The magnet 230 can move to a desired position according to the position of the external magnet 231 and a rotational direction and a rotational speed of the revolution plate 200. The magnet 230 influences magnetic force to adjacent portion in the microfluidic device so as to move or trap the magnetic beads.

An external energy source adjusting mean (not illustrated) in the microfluidic system of FIG. 10 can move the external energy source 60 installed facing the body of revolution 100 in a direction indicated by an arrow, in other words, a radial direction of the body of revolution 100. A mechanism of rectilinearly moving the external energy source 60 can be provided in various ways and is obvious to those of ordinary skill in the art. Therefore, a detailed description thereof is omitted.

Meanwhile, the microfluidic system includes the rotation operating unit 50 which rotates the body of revolution 100. The rotation operating unit 50 as illustrated in FIG. 10 is to settle the body of revolution 100 and to transmit a turning force. In addition, while not illustrated in FIG. 8, a motor and related parts thereof for the body of revolution 100 to be constantly rotated and reversely rotated can be included in the microfluidic system. A detailed description of the configuration of the rotation operating unit 50 is omitted. The external energy source 60 can irradiate an electromagnetic wave concentrically on the selected region on the body of revolution 100 of the microfluidic device with the support of the external energy source adjusting means (not illustrated) and the rotation operating unit 50.

For example, when the phase-change valve 31 which should be operated at a certain point of time is selected, the position of the phase-change valve (not illustrated) is known at the starting point of irradiating the external energy source 60 and $\Delta (r,\theta)$ (not shown), which is a deviation from the laser light source 60 to the phase-change valve, is obtained. $\Delta\theta$ is a distance to be moved in the rotation direction and $\Delta r$ is a distance to be moved in the radial direction of the body of the revolution 100 In addition, the body of revolution 100 can be reversely rotated by $\Delta\theta$ using the rotation operating unit 50 and the external energy source 60 can be moved toward a radial direction of the body of revolution 100 by $\Delta r$ using the external energy source adjusting means (not illustrated).

Figure 11:
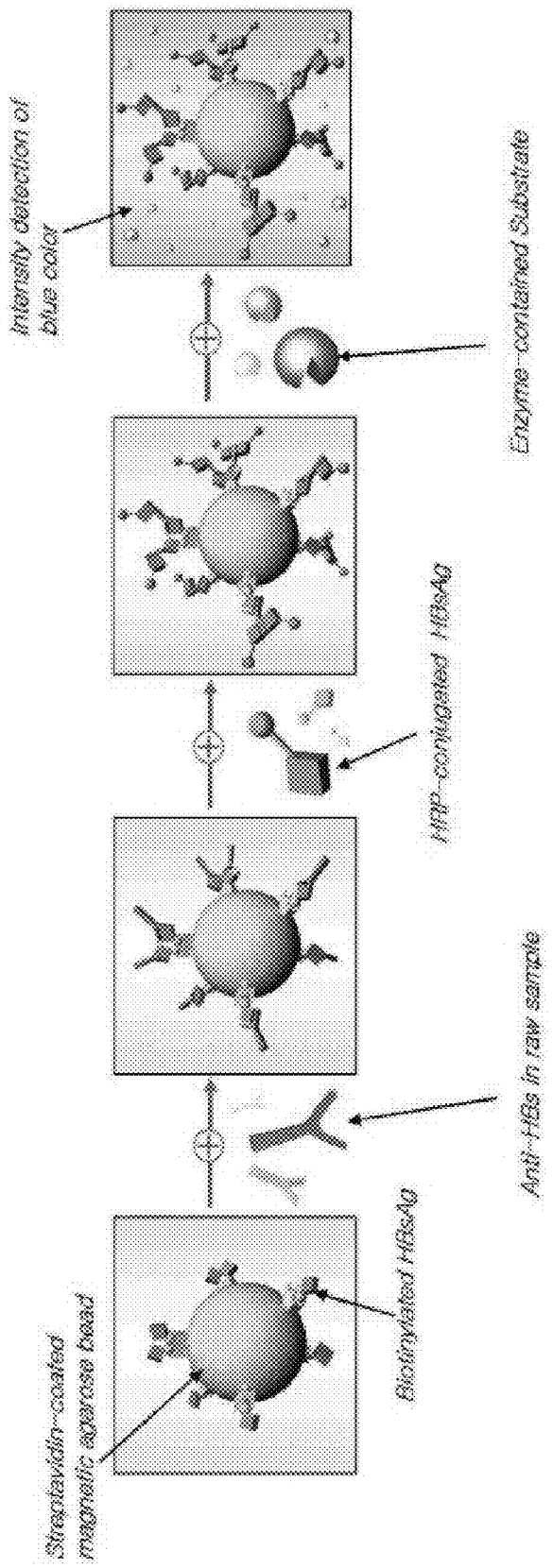
FIG. 11 is a series of schematic diagrams illustrating a process of an immunoassay using beads performed in a microfluidic device according to an embodiment of the present invention.

FIG. 11 is a series of schematic diagrams illustrating a process of an immunoassay using beads performed in a microfluidic device according to an embodiment of the present invention. First, beads including capture probes on the surface thereof, the capture probes having a unique affinity for specific target protein, are prepared to collect specific target protein using the beads. In the current embodiment of the present invention, streptavidin is coated onto the surface of the magnetic beads, the magnetic beads including a core formed of magnetic materials and a shell formed of agarose to surround the core, and biotinylated HBsAg (Hepatitis virus B surface antigen) is adhered onto the surface of the magnetic beads as the capture probe.

When the beads prepared as above are mixed with the sample including Anti-HBs (Hepatitis virus B surface antibody), Anti-HBs binds to HBsAg of the capture probe. Here, when HBsAg (secondary antibody) conjugated to HRP is added as the detection probe, HBsAg of the detection probe binds to Anti-HBs. Accordingly, when the beads in which (HBsAg)-(Anti-HBs)-(HBsAg-HRP) binding is formed on the surface of the beads are washed using a buffer solution, free detection probes are all washed off and the detection probes bonded to the beads only remain as above.

When the beads (which are) washed as above are mixed with materials which can express an optical signal due to a HRP action, for example, a substrate solution including an substrate and an enzyme, a transparent material included in the substrate expresses color (for example, blue) by an enzymatic reaction so as to express an optical signal. Since the optical signal is detected optically, presence of a target protein such as Anti-HBs in the sample can be detected. However, the above process is only an example. As another example, when a detection probe including fluorescein isothiocyanate (FITC) is used, optical detection through fluorescence manifestation is possible without additional reaction with a substrate solution.

Figure 12A:
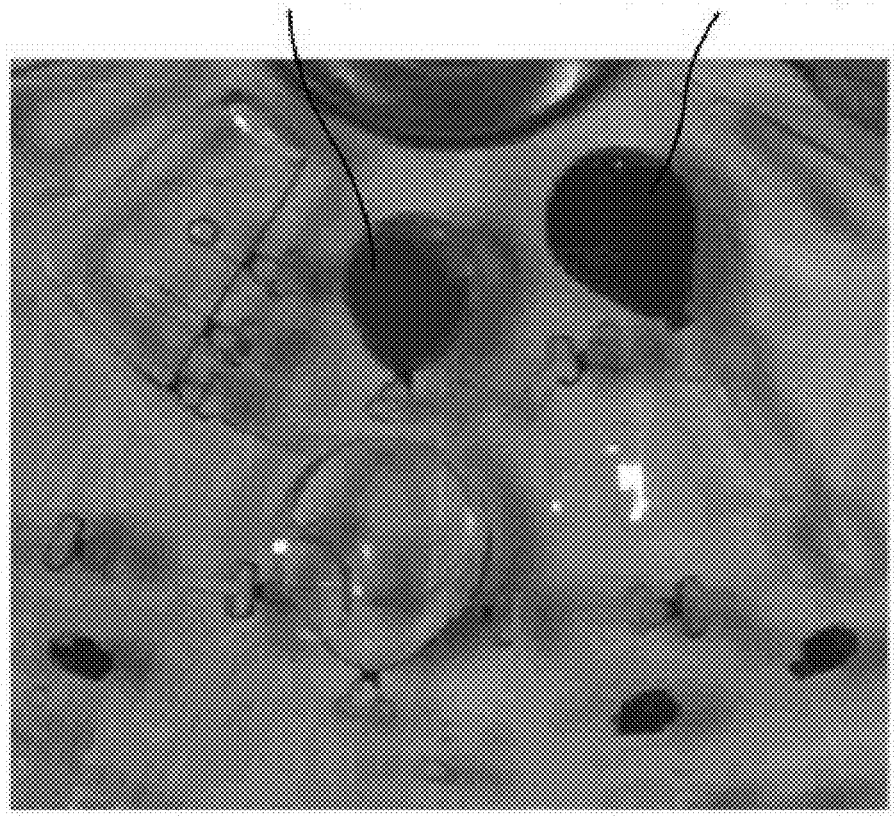
FIGS. 12A through 12P are photographic images illustrating a process of detecting Hepatitis virus B surface antibody (Anti-HBs) using a microfluidic device according to an embodiment of the present invention.
Figure 12B:
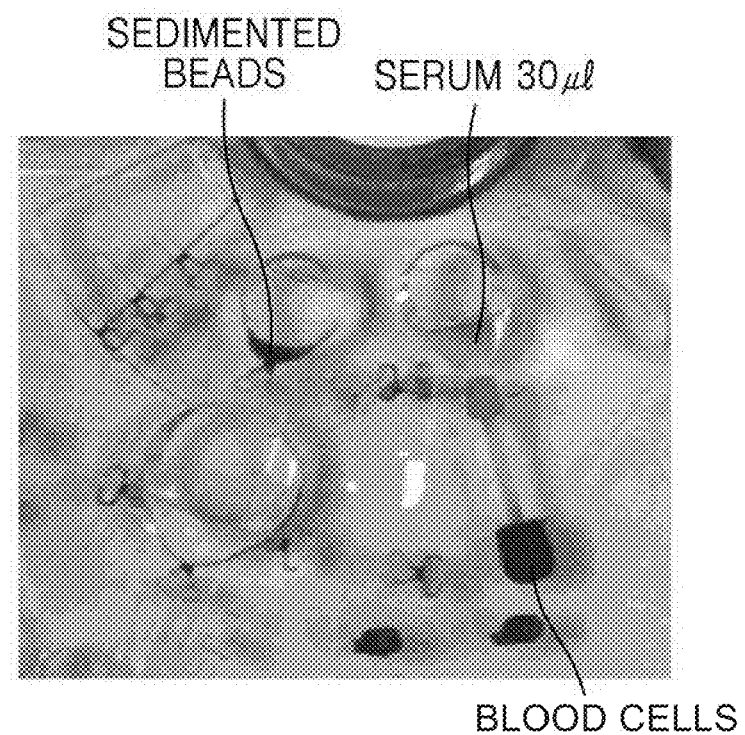
Figure 12C:
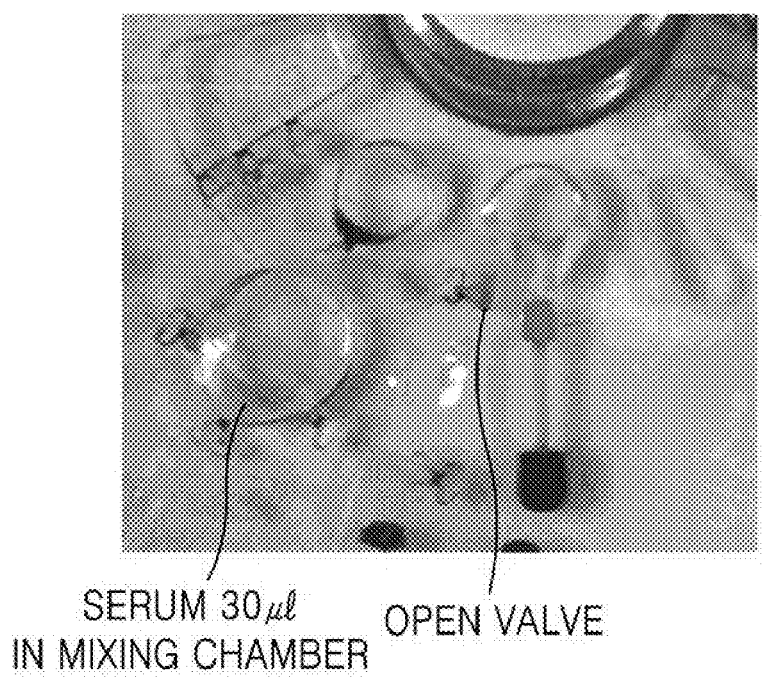
Figure 12D:
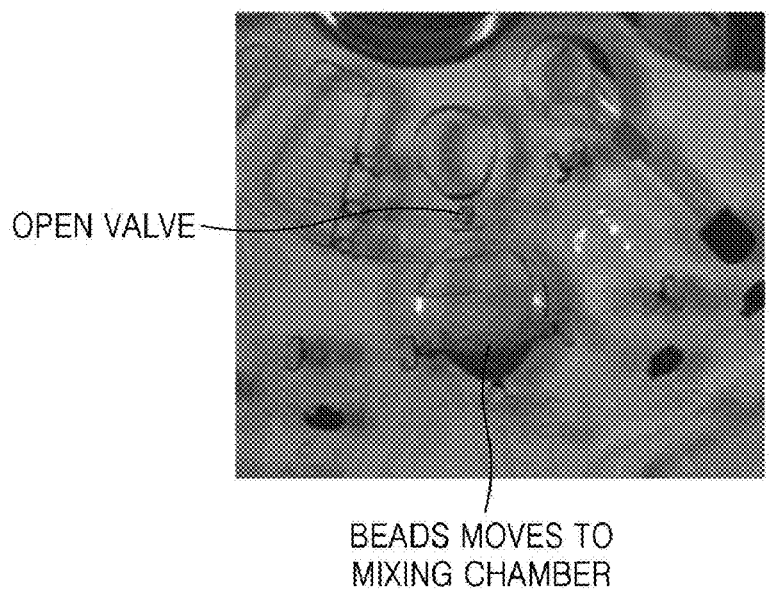
Figure 12E:
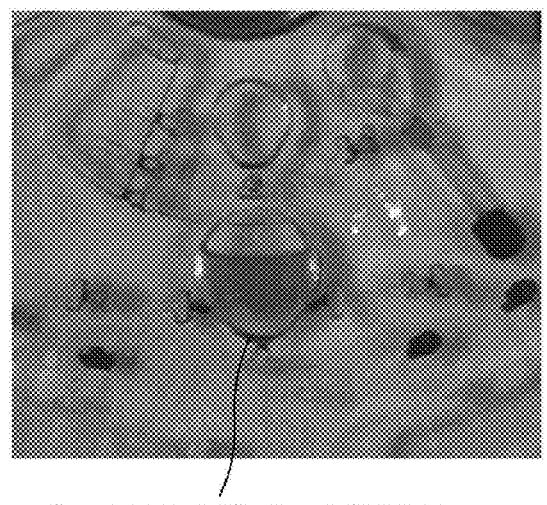
Figure 12F:
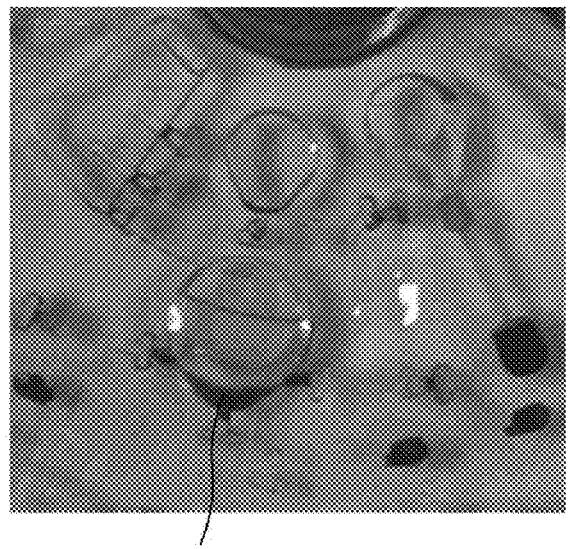
Figure 12G:
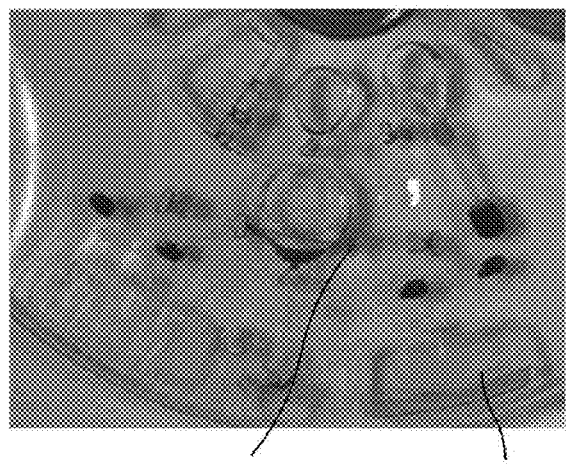
Figure 12H:
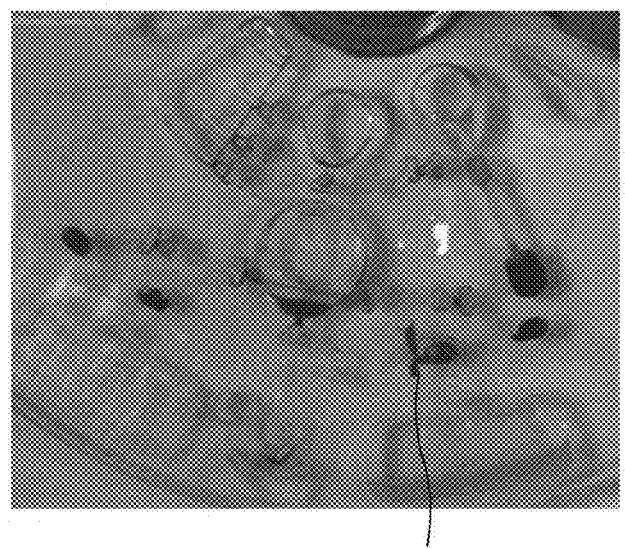
Figure 12I:
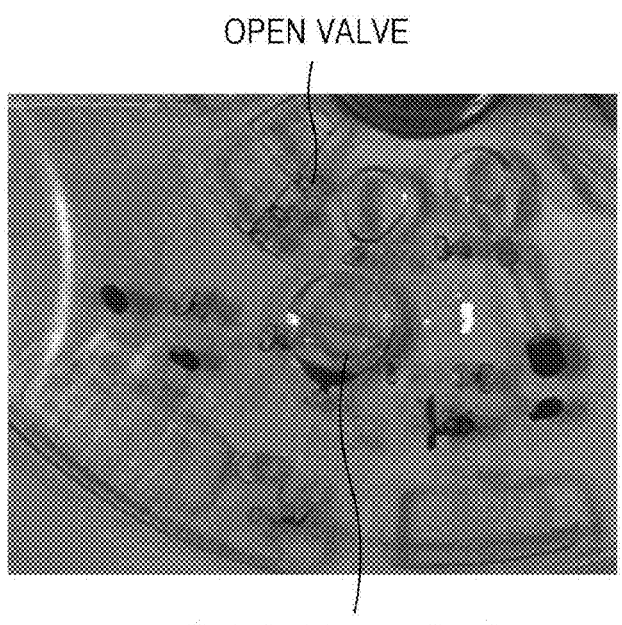
Figure 12J:
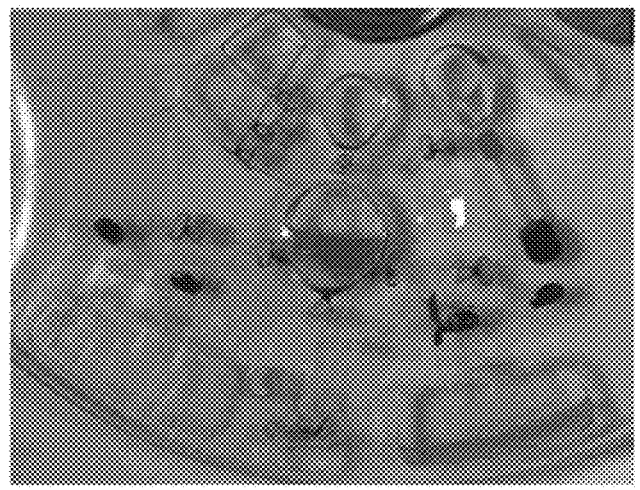
Figure 12K:
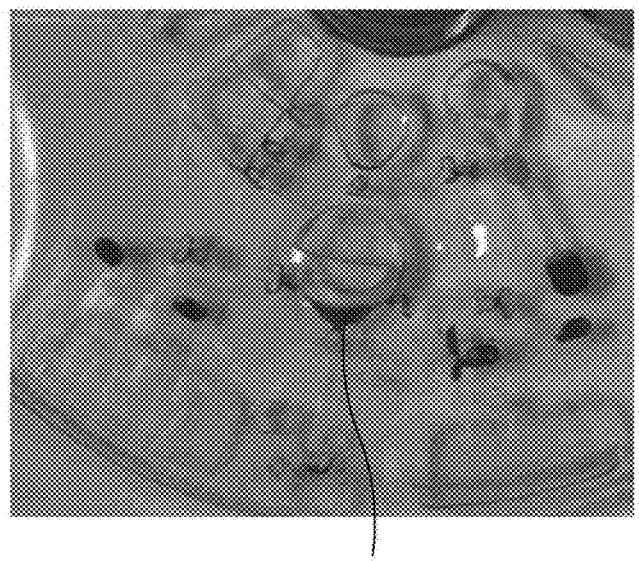
Figure 12L:
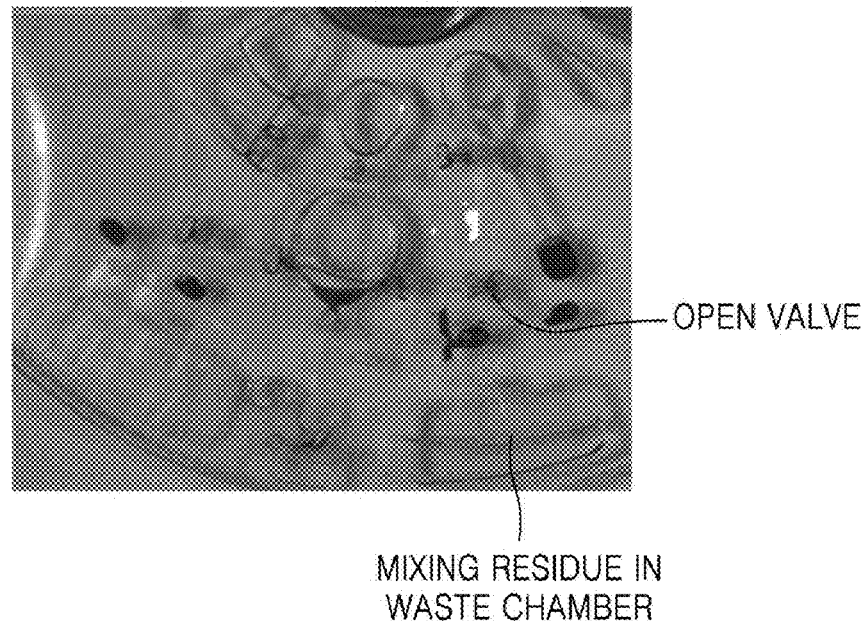
Figure 12M:
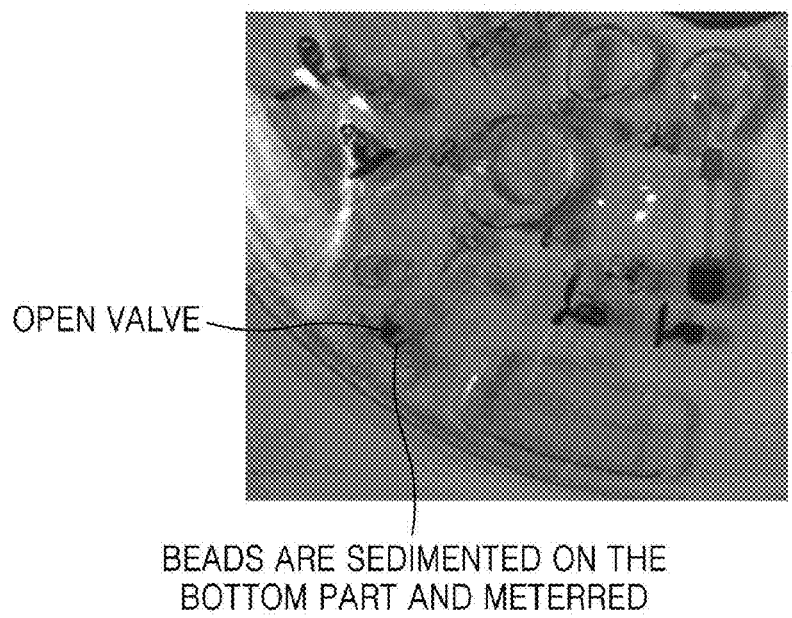
Figure 12N:
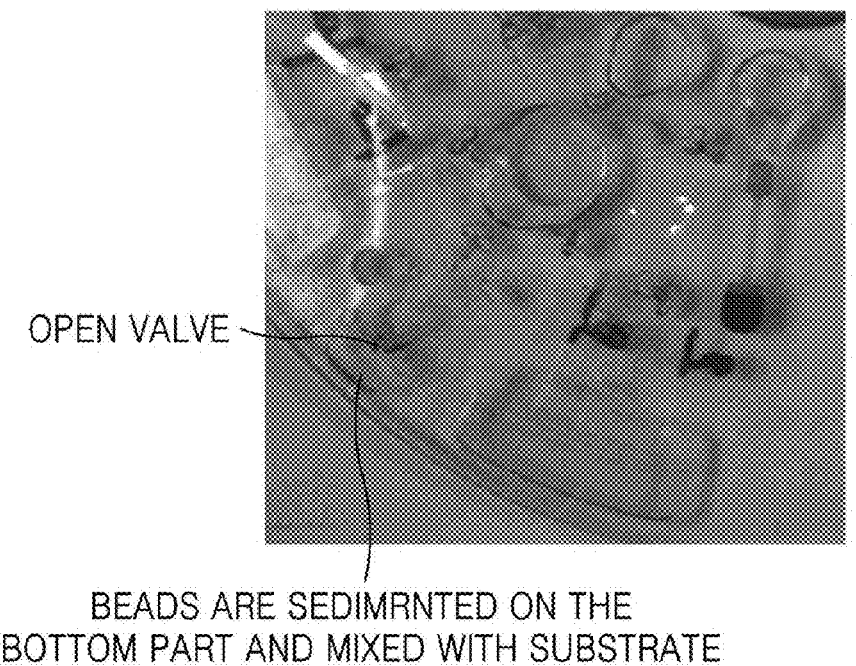
Figure 12O:
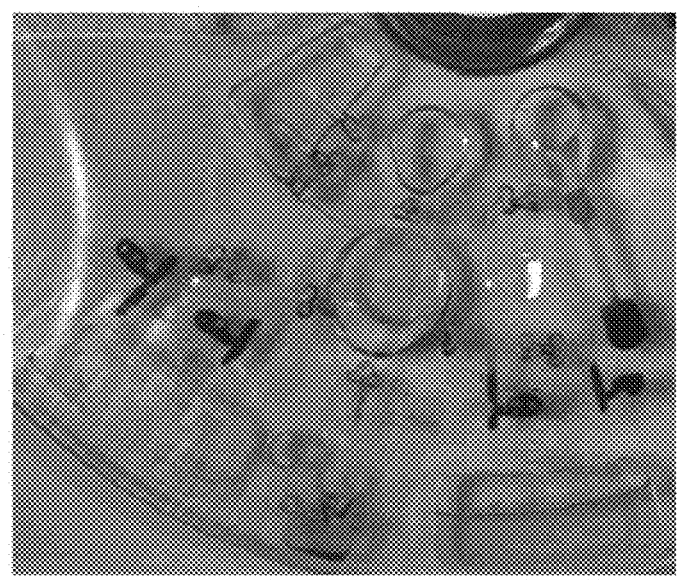
Figure 12P:
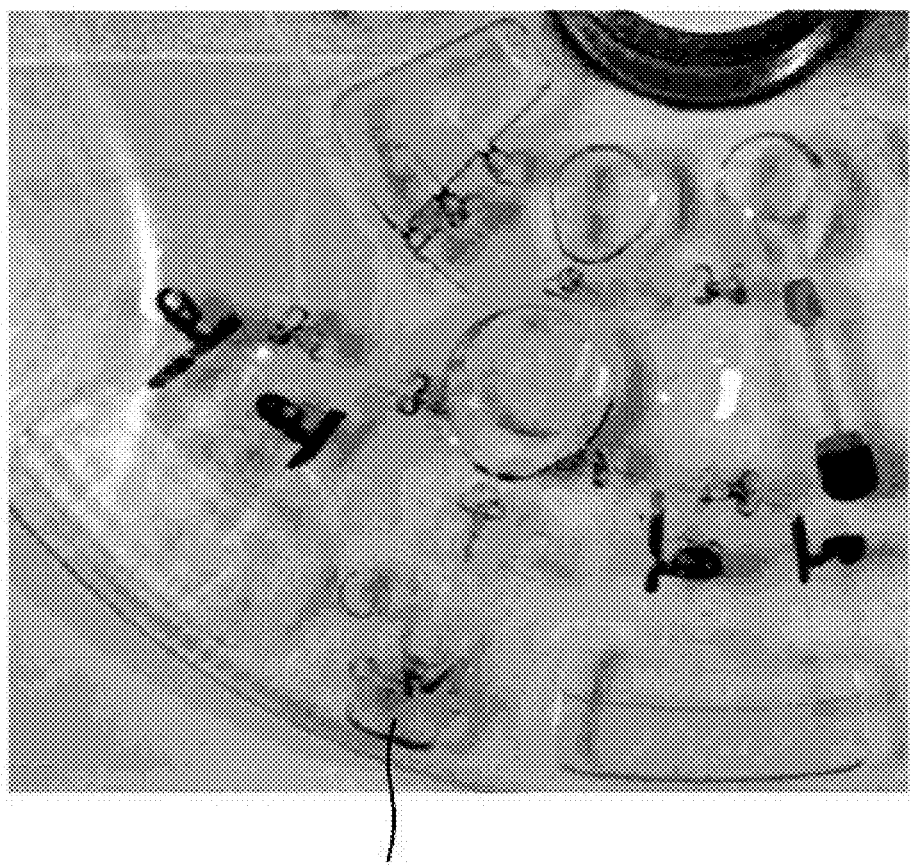

FIGS. 12A through 12P are photographic images illustrating a process of detecting Anti-HBs using a microfluidic device according to an embodiment of the present invention. The process described in FIG. 11 is performed in the microfluidic device of FIG. 4 and is illustrated in FIGS. 12A through 12P.

As described above, 100 µl of a bead solution including the beads on which HBsAg is adhered was injected into the bead chamber, and 100 µl of whole blood was injected into the sample chamber as a sample (FIG. 12A). While the body of revolution was rotated, the sample was separated into blood cell and serum using the centrifuging unit (FIG. 12B). The phase-change valve 31 was opened using the external energy source and 30 μl of serum was transferred into the mixing chamber. A detection probe solution injected into the mixing chamber in advance and the serum were mixed (FIG. 12C). The valve connecting with the bead chamber was opened, and the bead solution was transferred into the mixing chamber (FIG. 12D). While the body of revolution was alternately rotated in clockwise and ant-clockwise directions using the rotation operating unit, the beads, the sample, and the detection probe solution were reacted. In this case, the temperature of the mixing chamber may maintain similar to in vivo condition using the external energy source (FIG. 12E). Then, beads contained in the mixing chamber were precipitated using centrifugal force (FIG. 12F).

The channel connecting first with the waste chamber was opened to discharge residual sample (supernatant separated from the beads) to the waste chamber, wherein the residual sample is obtained after the reaction (FIG. 12G). The channel was closed again (FIG. 12H) and the channel connecting the buffer channel and the mixing chamber was opened to transfer the buffer solution to the mixing chamber (FIG. 12I). The body of revolution was alternately rotated in clockwise and ant-clockwise directions again to wash the beads contained in the mixing chamber for 1 minute using the buffer solution (FIG. 12J). After the beads were precipitated (FIG. 12K), another channel connecting with the waste chamber was opened to discharge residual buffer solution, wherein the buffer solution completes washing the beads (FIG. 12L). As described above, when a capacity of the buffer chamber is large and the channel including the valves disposed at each water level is connected with the buffer channel, the process illustrated in FIGS. 12I through 12L can be repeated. In other words, the beads can be washed many times.

Next, the outlet valve of the mixing chamber was opened and the washed beads were transferred to the optical signal emission chamber 16 (FIGS. 12M and 12N). The body of revolution was alternately rotated in clockwise and ant-clockwise directions and the substrate solution contained in the optical signal emission chamber and the beads were mixed to induce an optical signal (FIG. 12O). In this case, the temperature of the optical signal emission chamber can be also raised similar to a temperature of a biomaterial using the external energy source. The beads precipitated in the optical signal emission chamber and an optical signal due to a reaction between the detection probe and the substrate was detected using the light detecting unit (FIG. 12P).

As described above, the microfluidic device including a plurality of microfluidic structures and the microfluidic system including the microfluidic device according to the present invention can detect a target biomaterial, e.g., a protein of interest from biomaterial samples, through a series of processes performed quickly in the microfluidic structures such as injecting a sample into the microfluidic device. Therefore, an immunoassay performed using a conventional (Enzyme-Linked ImmunoSorbent Assay (ELISA) process which requires much effort from those of ordinary skill in the art is simplified and thus, time and effort can be significantly saved. In addition, target protein can be detected using a small amount of samples only.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:
1. A microfluidic device comprising:
a body of revolution having a rotation center and a circumference;
a microfluidic structure disposed in the body of revolution comprising a plurality of chambers, channels connecting the chambers to each other and forming a path of fluid flow between the chambers, and valves disposed in the channels to control the fluid flow, the microfluidic structures transmitting fluid using centrifugal force due to rotation of the body of revolution, wherein one of the plurality of chambers receives a fluid biological sample;
beads having a first probe to capture a target molecule from a fluid biological sample, the first probe selectively binds to the target molecule; and
a fluid containing a second probe selectively binding to the target molecule and including a substance emitting an optical signal,
wherein the microfluidic structure comprises:
a sample chamber which contains a sample solution containing the fluid biological sample;
a buffer chamber which contains a buffer solution;
a mixing chamber which is fluid connected to the sample chamber, the buffer chamber through the channel; which receives a solution containing the second probe and a bead solution containing the beads; which comprises an inlet to receive a fluid and an outlet to discharge the fluid, the outlet being disposed with a greater distance from the rotation center of the body of revolution than the inlet, and the outlet being provided with a valve to control a flow of the fluid discharged from the mixing chamber; and in which the sample and the beads are brought into contact with each other and the second probe to produce a bead-target molecule-second probe complex, if the fluid biological sample contains the target molecule; and separates the bead-target molecule-second probe complex;
a waste chamber which is fluid connected to the outlet of the mixing chamber through a channel, the waste chamber receiving the fluid discharged from the mixing chamber by changes of phases of a valve; and
an optical signal emission chamber connected to the outlet of the mixing chamber through a channel, in which a substrate solution is brought into contact with the bead-target molecule-second probe complex to generate an optical signal.

2. The microfluidic device of claim 1, wherein the mixing chamber is disposed with a greater distance from the center of the body of revolution than the sample chamber and the buffer chamber, and is disposed with a smaller distance from the center of the body of revolution than the waste chamber and the optical signal emission chamber.

3. The microfluidic device of claim 1, wherein the channel connecting the mixing chamber and the waste chamber is connected such that a space can be provided in the mixing chamber where the beads can be collected, between a part connected to the channel and the outlet of the mixing chamber.

4. The microfluidic device of claim 3, wherein the channel connecting the mixing chamber and the waste chamber comprises a valve which can open and close.

5. The microfluidic device of claim 4, wherein the channel connecting the mixing chamber and the waste chamber can open and close at least two times.

6. The microfluidic device of claim 1, wherein the channels connecting the buffer chamber and the mixing chamber are connected corresponding to various levels of a fluid in the buffer chamber and each channel comprises valves, each of which is operated independently.

7. The microfluidic device of claim 1, wherein the beads are magnetic beads and further comprises magnetic field forming materials which are disposed at a location which allows the optical signal emission chamber to draw and concentrate the magnetic beads contained in the optical signal emission chamber by magnetic force of the magnetic field forming materials.

8. The microfluidic device of claim 1, further comprising a centrifuging unit connected to a channel which connects the sample chamber and the mixing chamber, the centrifuging unit centrifuging the fluid biological sample contained in the sample chamber, prior to discharging the fluid biological sample into the mixing chamber.

9. The microfluidic device of claim 1, wherein the optical signal emission chamber receives the substrate solution, which is brought into contact with the bead-target molecule-second probe complex to generate an optical signal.

10. The microfluidic device of claim 9, wherein the mixing chamber receives a termination solution which stops reaction of the optical signal emission material and the substrate solution.

11. A microfluidic system comprising:
the microfluidic device of claim 1;
a rotation operating unit which rotates the body of revolution of the microfluidic device; and
a light detecting unit which detects an optical signal of the microfluidic device.

12. The microfluidic device of claim 1, wherein the beads are non-magnetic beads, which are located at the mixing chamber and generate the optical signal when the substrate solution is brought into contact with the bead-target molecule-second probe complex.

* * * * *